United States Patent

Sakamoto et al.

Patent Number: 5,283,244
Date of Patent: Feb. 1, 1994

[54] FUSED PYRAZINE DERIVATIVES

[75] Inventors: Shuichi Sakamoto, Ushiku; Junya Ohmori, Tsukuba; Hirokazu Kubota, Edosaki; Masao Sasamata, Ibaraki; Masamichi Okada, Tsukuba; Kazuyuki Hidaka, Kashiwa, all of Japan

[73] Assignee: Yamanouchi Pharmaceutical Co., Ltd., Tokyo, Japan

[21] Appl. No.: 50,225

[22] PCT Filed: Nov. 1, 1991

[86] PCT No.: PCT/JP91/01498

§ 371 Date: May 5, 1993

§ 102(e) Date: May 5, 1993

[87] PCT Pub. No.: WO92/07847

PCT Pub. Date: May 14, 1992

[30] Foreign Application Priority Data

Nov. 6, 1990 [JP] Japan ................ 2-300879
Jan. 11, 1991 [JP] Japan ................ 3-069592
Mar. 29, 1991 [JP] Japan ................ 3-133828
Jun. 27, 1991 [JP] Japan ................ 3-183248

[51] Int. Cl.$^5$ ................ A61K 31/495; A61K 31/535; C07D 403/02; C07D 413/14
[52] U.S. Cl. ................ 514/249; 514/234.5; 514/250; 544/116; 544/119; 544/350; 544/354
[58] Field of Search ............... 544/116, 119, 350, 354; 514/234.5, 249, 250

[56] References Cited

U.S. PATENT DOCUMENTS 5,028,606 7/1991 Venet et al. ................ 544/354

Primary Examiner—Robert W. Ramsuer
Attorney, Agent, or Firm—Burgess, Ryan & Wayne

[57] ABSTRACT

The present invention is a pyrazine derivative which has glutamate receptor antagonizing activity, represented by formula:

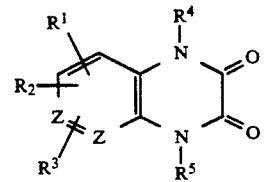

wherein Z represents C or N, provided that two Zs are not N atoms at the same time; $R^1$ represents:

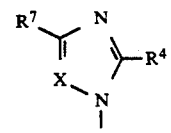

wherein

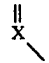

represents

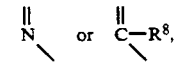

$R^6$ represents H or alkyl, and $R^7$ and $R^8$ represent each H, alkyl, nitro or phenyl, or alternatively $R^7$ and $R^8$ are combined together to represent butadienylene or 1,4-butylene; $R^2$ and $R^3$ represent each H, F, cyano, acyl, nitro, alkyl, morpholino or one of said species of $R^1$; $R^4$ and $R^5$ represent each H, hydroxyl, alkyl, cycloalkyl, heterocycle, phenyl, or Y-substituted alkyl; Y represents hydroxyl, acyloxy, F-substituted methyl, cycloalkyl, tetrahydrofuryl, carboxyl, alkoxycarbonyl or (Abstract continued on next page.)

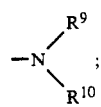
$R^9$ and $R^{10}$ represent each H or alkyl, or alternatively $R^9$ and $R^{10}$ are combined together to represent a 5- or 6-membered cyclic group which may contain oxygen atom(s).
14 Claims, No Drawings

FUSED PYRAZINE DERIVATIVES

TECHNICAL FIELD

The present invention relates to a fused pyrazine derivative or a salt thereof, which has glutamate receptor antagonizing activity, particularly NMDA-glycine receptor antagonizing activity and AMPA receptor antagonizing activity.

BACKGROUND ART

Certain amino acids such as L-glutamic acid and L-aspartic acid are known to be central neurotransmitters. It is said that accumulation of these excitatory amino acids results in a persistent overstimulation of the nerves which, in turn, causes neuronal degeneration and mental and motor dysfunctions as are observed in Huntington's chorea, Parkinson's disease, epilepsy and senile dementia, or after cerebral ischemia, oxygen deficiency or hypoglycemia.

Therefore, it is by now considered that drugs which may modulate abnormal actions of these excitatory amino acids are useful for the treatment of neuronal degeneration and mental disease.

Excitatory amino acids exert their effects via the specific receptors present in the post- or presynaptic regions. These receptors have been classified into the following five groups based on electrophysiological and neurochemical evidence.

1) NMDA (N-methyl-D-aspartate) receptor
2) AMPA [2-amino-3-(3-hydroxy-5-methyl-4-isoxazole)-propionic acid] receptor
3) Kainate receptor
4) Metabotropic glutamate receptor
5) AP-4 (2-amino-4-phosphobutanoic acid) receptor L-Glutamic acid and L-aspartic acid activate the above-mentioned receptors to transmit stimuli. Permitting an excessive amount of NMDA, AMPA or kainate to act on nerves causes neuropathy. It is reported that 2-amino-5-phosphonovalerianic acid and 2-amino-7-phosphonoheptanoic acid, both of which are selective antagonists of NMDA receptor, were effective in NMDA-induced neuropathy and in animal models of epilepsy or brain ischemia (JPET, 250, 100 (1989); JPET, 240, 737 (1987); Science, 226, 850 (1984)).

While NMDA receptor is reported to be allosterically functioning by glycine receptor (EJP, 126, 303 (1986)), HA-966 which is a glycine receptor antagonist is reported to be effective in an animal model of brain ischemia (1989 Congress of American Society of Neuroscientists).

NBQX (6-nitro-7-sulfamoylbenzo[f]quinoxaline), a selective antagonist of AMPA receptor, is also reported to be effective in an animal model of brain ischemia (Science, 247, 571 (1990)). On the other hand, there is no report with respect to selective antagonists of kainate, metabotropic glutamate and AP-4 receptors.

DISCLOSURE OF INVENTION

The object of the present invention is to provide a diketoquinoxaline or diketopyridopyrazine compound having glutamate receptor antagonizing activity, particularly NMDA-glycine receptor and/or AMPA receptor antagonizing activity. Several diketoquinoxaline derivatives having NMDA-glycine antagonizing and-/or AMPA antagonizing activity have been reported (JP-A-63-83074, JP-A-63-258466, JP-A-1-153680, JP-A-48578, JP-A-2-221263, and JP-A-2-221264; the term "JP-A" as used herein means an "unexamined published Japanese patent application"). However, the compound of the present invention is a novel compound which has structural characteristic that it has an imidazolyl or triazolyl group on the diketoquinoxaline or diketopyridopyrazine ring.

Thus, the present invention relates to a pyrazine derivative represented by the general formula:

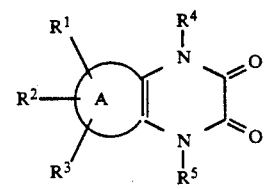

wherein ring A represents a benzene ring of the formula

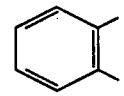

or a pyridine ring of the formula

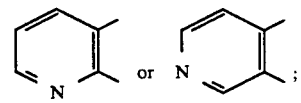

$R^1$ represents

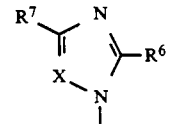

(X represents a nitrogen atom, or a carbon atom substituted by $R^8$, $R^6$ represents a hydrogen atom or a lower alkyl group, $R^7$ and $R^8$ are the same or different and each represents hydrogen, lower alkyl, nitro or phenyl, or $R^7$ and $R^8$ are combined together to represent butadienylene (—CH=CH—CH=CH—) or 1,4-butylene (—CH$_2$—CH$_2$—CH$_2$—CH$_2$—)); $R^2$ and $R^3$ are the same or different and each represents hydrogen, fluoro, cyano, lower acyl, nitro, unsubstituted or fluorine-substituted lower alkyl, morpholino, or one of said species of $R^1$ which may be either the same as or different from $R^1$; $R^4$ and $R^5$ are the same or different and each represents hydrogen, hydroxyl, $C_{1-10}$ straight-chain or branched alkyl, $C_{5-8}$ cycloalkyl which may be substituted by amino, a nitrogen-containing 5- or 6-membered heterocyclic group which may be substituted by lower alkyl and which may be bridged by 1 to 3 methylene group(s), phenyl, or Y-substituted $C_{1-6}$ straight-chain or branched alkyl; Y represents hydroxyl, lower acyloxy, fluorine-substituted methyl, $C_{5-8}$ cycloalkyl, tetrahydrofuryl, carboxyl, lower alkoxycarbonyl, or

($R^9$ and $R^{10}$ are the same or different and each represents hydrogen or lower alkyl, or alternatively $R^9$ and $R^{10}$ are combined together to represent a 5- or 6-membered cyclic group which may contain oxygen), or a salt thereof.

The "nitrogen-containing 5- or 6-membered heterocyclic group" in the above definition means piperidinyl and pyrrolidinyl and s on. The "nitrogen-containing 5- or 6-membered heterocyclic group which is bridged by 1 to 3 methylene group(s)" means quinuclidinyl and so on.

The "5- or 6-membered cyclic group which may contain oxygen" represented by $R^9$ and $R^{10}$ combined together means morpholino, among others.

The "lower alkyl group" in the above definition means a straight-chain or branched $C_{1-6}$ hydrocarbon group. Typical groups of the same are methyl, ethyl, butyl, isopropyl and so on. The "lower acyl group" means, formyl, acetyl, propionyl, butanoyl and so on.

While the above compound (I) may occur as stereoisomers or tautomers according to substituents, such isomers in an isolated form as well as in mixtures also fall within the scope of the compound of the present invention.

The salt of the above compound (I) includes salts with inorganic acids such as hydrochloric acid, hydrobromic acid, sulfuric acid, etc., salts with organic acids such as fumaric acid, tartaric acid, alkanesulfonic acids, arylsulfonic acids, etc. and salts with inorganic bases such as sodium hydroxide, potassium hydroxide, etc. and salts with organic bases such as diethylamine and so on.

Production Process

The compound of the present invention can be produced in accordance with the following reaction schema.

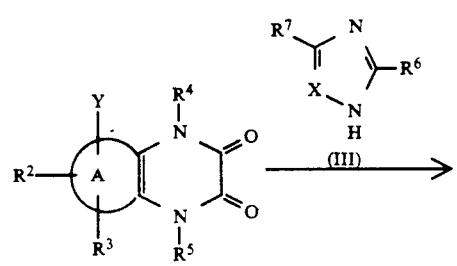

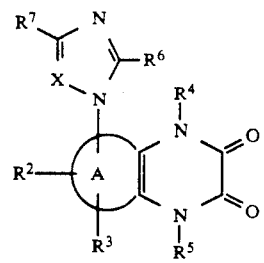

(I)

(wherein Y means a halogen atom; ring A, X, $R^4$, $R^2$, $R^3$, $R^7$, $R^5$ and $R^6$ are as defined hereinbefore).

For conducting the above reaction, halide (II) and either imidazole or triazole compound (III) are reacted in stoichiometric amounts. This reaction is generally conducted in a solvent, such as dimethylformamide, dimethyl sulfoxide, acetonitrile, acetone, tetrahydrofuran or the like, under warming. The reaction may be accelerated by adding a base such as sodium hydroxide, potassium hydroxide or the like.

The compound of the present invention can also be produced in accordance with the following reaction schema.

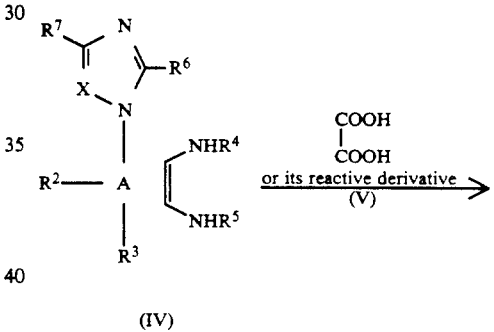

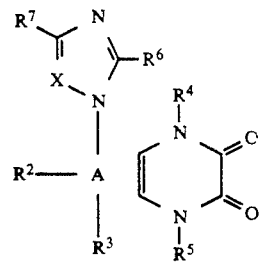

(I)

This production process is carried out by reacting diamino compound (IV) with an equimolar or excess of oxalic acid or a reactive derivative thereof (V) at room temperature or under warming. The reactive derivative of oxalic acid may, for example, be the corresponding salt, ester, hydrate, anhydride or acid chloride. This reaction is generally conducted in an aqueous solvent or an alcoholic solvent. It is preferable to add an acid such as hydrochloric acid or the like to accelerate the reaction.

For the production of compound (I,), the following alternative process can be used.

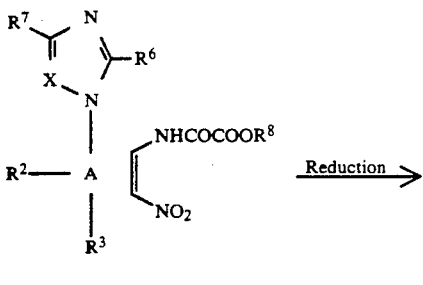

(VI)

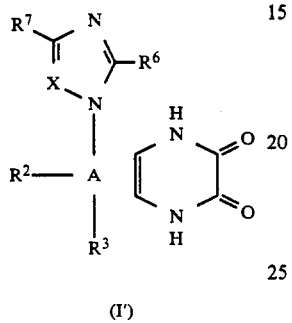

(I')

(wherein R⁸ represents a lower alkyl group; the other symbols are as defined hereinbefore).

This reaction, involving reductive cyclization of lower alkoxalylamino compound (VI), can be carried out by the catalytic reduction method using Raney nickel or the like as the catalyst.

A still another process for the production of the compound of the present invention comprises introducing a new substituent group into ring A of the compound obtained by any of the above processes or exchanging substituents. The compound of the invention in which $R^1$ is a nitro group, for instance, can be obtained by nitrating the corresponding compound in which $R^1$ is hydrogen. This nitration reaction can be conducted by a process comprising reacting the compound not having a nitro group with nitric acid or a salt thereof under acidic conditions in the presence of sulfuric acid or acetic anhydride-acetic acid or sulfuric acid-acetic anhydride-acetic acid or by a process comprising heating said compound together with nitronium tetrafluoroborate in an organic solvent such as sulfolane.

The compound of the present invention has a strong affinity for NMDA-glycine receptor and/or AMPA receptor. The action on NMDA receptor ([³H]-MK-801 binding inhibitory activity) was observed at the concentration of 1 µM. The AMPA receptor binding inhibitory activity, for example of the compound of Example 8, was 96% at 1 µM and its Ki value was 21 nM. The compounds of Examples 9 and 15 inhibited audiogenic convulsions at 3 mg/kg when given 15 minutes before sound stimulation.

Furthermore, when the compound of this invention, for example the compound of Example 15, was administered 60, 70 and 85 minutes after 5-minute ischemia, it exhibited 60% neuron protecting activity with a lesion score of 1.2.

Experimental Methods

The activity of the compound of the present invention on NMDA-glycine receptor ([³H]-MK-801 binding inhibitory activity) and the [³H]-AMPA binding inhibitory activity, audiogenic convulsion inhibitory activity and neuron protecting activity of the compound were determined by the following methods.

Effect on NMDA-Glycine Assay Receptor Assay of [³H]-MK-801 Binding Inhibitory Activity]

The binding activity and antagonistic activity with respect to NMDA-glycine receptors were determined by a binding assay using [³H]-MK-801 as the ligand.

Determination of [³H]-AMPA Binding Activity

A mixture (0.5 ml) of about 45 nM [³H]-AMPA (2-amino-3-(3-hydroxy-5-methyl-4-isoxazole)propionic acid), about 300 mg of rat cerebral membrane specimen and the test compound was allowed to react on ice-water for 45 minutes. The amount of [³H]-AMPA bound to quisqualic acid receptors was determined by the filtration method. Of the total amount of binding, the portion substituted for by 10 µM quisqualic acid was regarded as specific binding. The test compound was evaluated by determining the percentage inhibition of the specific binding.

Determination of Audiogenic Convulsion Inhibitory Activity in DBA/2 Mice

Ten male mice, 21-28 days old, were placed in a soundproof box and loaded with a sound stimulus of 12 KHz and 120 dB for 1 minute or until the mice developed tonic convulsions.

The test compound was suspended in 0.5% methylcellulose solution or dissolved in physiological saline and administered intraperitoneally 45 or 15 minutes before sound stimulation.

The effect of the test compound was evaluated according to the onset of convulsion and the minimum effective dose (MED) was determined.

Neuron-Protective Action in the Hippocampus

The protective action on nerve cell necrosis due to cerebral ischemia was tested using a gerbil model of ischemia constructed by occlusion of the bilateral common carotid arteries.

Procedure

The bilateral common carotid arteries of the gerbil were occluded for 5 minutes under halothane anesthesia with the animal kept warm to avoid hypothermia and, then, the animal was allowed to recover from anesthesia. After 4 days, the brain was isolated and sections were prepared for histological examination of the degree of neuronal damage in the hippocampus CA1.

Method of Administration

The test compound, either suspended in 0.5% methylcellulose solution or dissolved in physiological saline, was administered intraperitoneally. Two dosage regimens were employed. In regimen 1, 30 mg/kg/dose was administered 45 and 15 minutes before ischemia and 5 minutes and 1, 2, 3, 6 and 24 hours after obtaining re-patency. In regimen 2, 30 mg/kg/dose was administered 60, 70 and 85 minutes after obtaining re-patency.

Method of Evaluation

Histopathological examination was performed using a light microscope. The degree of nerve cell impairment in the hippocampus CA1 area was rated on a 4-point scale of no lesion (score 0), slight necrosis (score 1), moderate necrosis (score 2) and complete necrosis (score 3).

The compound of this invention and salt thereof have glutamate receptor antagonizing activity, particularly antagonistic activity against one of or both of NMDA-glycine and/or AMPA receptors, inhibitory activity against the neurotoxic effect of excitatory amino acids, and anticonvulsant activity. Therefore, they are useful especially for preventing nerve degeneration and mental and motor dysfunctions in Huntington's chorea, Parkinson's disease, epilepsy and senile dementia or following cerebral ischemia, oxygen deficiency, hypoglycemia or convulsion.

The compound represented by formula (I) or a salt thereof is usually administered systemically or topically, for example orally or parenterally. The dosage may vary with age, body weight, clinical condition, therapeutic response, route of administration, treatment period and so on. For oral administration, the usual daily dosage for adults is 1 to 1000 mg, preferably 50 to 200 mg, to be administered in a single dose or in a few divided doses. For parenteral administration, 1 mg to 500 mg of the compound is administered intravenously in a single dose or in a few divided doses or by intravenous infusion over a period of 1 to 24 hours. Of course, as mentioned above, the dosage should vary depending on various conditions, sufficient efficacy may be obtained with a dosage lower than the above range.

EXAMPLES

The present invention is described in further detail with reference to Examples, but it should not deemed to be limited thereto. Examples of processes for the production of major starting materials for use in the examples are described below as Reference Examples.

Among the symbols used in the presentation of physicochemical data, NMR stands for nuclear magnetic resonance spectrum, MS for mass spectrum, m.p. for melting point and E.A. for elemental analysis.

REFERENCE EXAMPLE 1

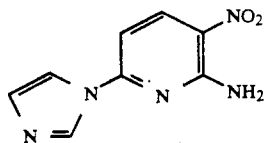

In 80 ml of N,N-dimethylformamide were dissolved 4.00 g of 2-amino-6-chloro-3-nitropyridine and 15.69 g of imidazole, and the solution was stirred at 120° C. overnight. After spontaneous cooling to room temperature, 100 ml of water was added and the resulting crystals were collected by filtration. The crystals were rinsed with a small amount of water and dried under reduced pressure to provide 3.76 g of 2-amino-6-imidazolyl-3-nitropyridine. Physicochemical properties:

NMR (DMSO-$d_6$: δ from TMS): 7.16 (d, 1H), 7.16 (q, 1H), 7.95 (t, 1H), 8.18 (br, 2H), 8.56 (d, 1H), 8.57 (d, 1H). MS (EI): 205 (M+).

REFERENCE EXAMPLE 2

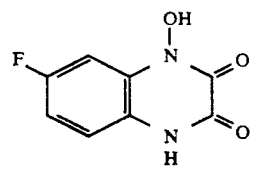

To a mixture of 5.6 g of 2-ethoxalylamino-5-fluoronitrobenzene and 170 ml of DMF was added 0.3 g of 10% Pd-C, and hydrogenation reaction was carried out at ordinary temperature and pressure. The reaction mixture was then filtered and concentrated under reduced pressure. The resulting residue was recrystallized from ethanol to provide 3.68 g (85%) of 7-fluoro-1-hydroxyquinoxaline-2,3-(1H,4H)-dione Physicochemical properties:

NMR (DMSO-$d_6$: δ from TMS): 6.93–7.31 (m, 3H), 11.83 (s, 1H), 12.1 (s, 1H). MS (FAB): 197 (M+1).

m.p.: 138°–140° C. (dec.) (EtOH).

| | E.A. (for $C_8H_5N_2O_3F$): | | |
|---|---|---|---|
| | C | H | N |
| Calcd. (%) | 48.99 | 2.57 | 14.28 |
| Found (%) | 48.79 | 2.68 | 14.16 |

REFERENCE EXAMPLE 3

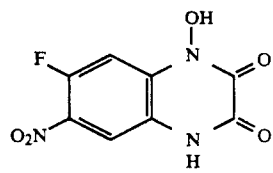

In 20 ml of sulfuric acid was dissolved 1.34 g of 7-fluoro-1-hydroxyquinoxaline-2,3-(1H,4H)-dione followed by addition of 0.76 g of potassium nitrate under ice-cooling. The mixture was cooled to at room temperature, and after 1 hour, the reaction mixture was poured in ice-water. The resulting crystals were recovered by filtration, rinsed with water and recrystallized from ethanol-water to provide 0.82 g (50%) of 7-fluoro-1-hydroxy-6-nitroquinoxaline-2,3-(1H,4H)-dione.

Physicochemical properties:

NMR (DMSO-$d_6$; δ from TMS): 7.50 (d, 1H), 7.91 (d, 1H), 12.20 (1H), 12.32 (1H). MS (EI): 241 (M+).

m.p.: 202° C. (dec.) (EtOH-$H_2O$)

| | E.A. (for $C_8H_4N_3O_5F$): | | |
|---|---|---|---|
| | C | H | N |
| Calcd. (%) | 39.85 | 1.67 | 17.43 |
| Found (%) | 40.24 | 1.80 | 17.18 |

REFERENCE EXAMPLE 4

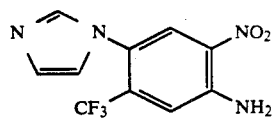

In 10 ml of DMF were dissolved 1.00 g of 4-fluoro-2-nitro-5-trifluoromethylacetanilide and 2.56 g of imidazole, and the solution was stirred at 150° C. for 3 hours. The reaction mixture was then diluted with 30 ml of water and the resulting crystals were recovered by filtration and purified by column chromatography chloroform-methanol=20:1) to provide 0.53 g (52%) of 4-(1-imidazolyl)-2-nitro-5-trifluoromethylaniline.

Physicochemical properties:
NMR (DMSO-$d_6$; δ from TMS): 7.05 (s, 1H), 7.31 (s, 1H), 7.61 (s, 1H), 7.75 (s, 1H), 7.95 (s, 2H), 8.04 (s, 1H). MS (EI): 272 (M+).

REFERENCE EXAMPLE 5

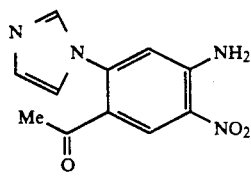

In 20 ml of DMF were dissolved 0.70 g of 4-amino-2-fluoro-5-nitroacetophenone and 1.20 g of imidazole, and the mixture was stirred at 130° C. for 1 hour. After spontaneous cooling, the reaction mixture was diluted with 60 ml of water. The resulting crystals were recovered by filtration and purified by column chromatography (chloroform-methanol=3:1) to provide 0.28 g (32%) of 4-amino-2-(1-imidazolyl)-5-nitroacetophenone.

Physicochemical properties:
NMR (DMSO-$d_6$; δ from TMS): 2.18 (s, 3H), 6.98 (s, 1H), 7.08 (s, 1H), 7.37 (t, 1H), 7.84 (s, 1H), 8.03 (br, 2H), 8.52 (s, 1H). MS (EI): 246 (M+).

REFERENCE EXAMPLE 6

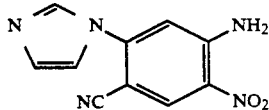

In 5 ml of DMF were dissolved 1 g of 4-amino-2-fluoro-5-nitrobenzonitrile and 1.1 g of imidazole, and the mixture was stirred at 100° C. for 1 hour. The reaction mixture was then diluted with water and the resulting crystals were recovered by filtration to provide 1.2 g of 4-amino-2-(1-imidazolyl)-5-nitrobenzonitrile. Physicochemical properties:
NMR (DMSO-$d_6$; δ from TMS): 7.11 (s, 1H), 7.18 (s, 1H), 7.61 (s, 1H), 8.10 (s, 1H), 8.21 (s, 2H), 8.64 (s, 1H). MS (EI): 229 (M+).

EXAMPLE 1

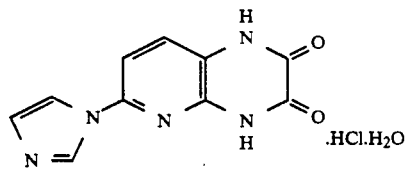

In a mixed solution of 40 ml of methanol and 2 ml of acetic acid was suspended 3.68 g of 2-amino-6-imidazolyl-3-nitropyridine. Then, 0.20 g of 10% palladium-on-carbon was added and hydrogenation was carried out at atmospheric pressure. The reaction mixture was filtered and the filtrate was concentrated under reduced pressure. To the residue were added 24 ml of 4N-hydrochloric acid and 1.61 g of oxalic acid and the mixture was refluxed overnight. After spontaneous cooling to room temperature, the resulting crystals were recovered by filtration and recrystallized from N,N-dimethylformamide to provide 2.30 g of -imidazolylpyrido[2,3-b]pyrazine-2,3-dione hydrochloride monohydrate.

Physicochemical properties:
NMR (DMSO-$d_6$; δ from TMS): 7.80 (s, 2H), 7.88 (q, 1H), 8.24 (t, 1H), 9.75 (t, 1H), 12.43 (s, 1H), 12.67 (s, 1H). MS (FAB): 230 (M+ +1).
m.p.: >300° C. (DMF).

| E.A. (for $C_{10}H_7N_5O_2$.HCl.$H_2O$.0.1Me$_2$NCHO): | | | | |
| --- | --- | --- | --- | --- |
| | C | H | N | Cl |
| Calcd. (%) | 42.52 | 3.71 | 24.55 | 12.18 |
| Found (%) | 42.46 | 3.52 | 24.84 | 12.02 |

EXAMPLE 2

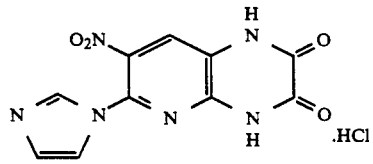

In 10 ml of sulfolane was dissolved 1.01 g of -imidazolylpyrido[2,3-b]pyrazine-2,3-dione hydrochloride monohydrate followed by addition of 1.35 g of nitronium tetrafluoroborate, and the mixture was stirred at 120° C. for 4 hours. The reaction mixture was then allowed to cool to room temperature, diluted with 10 ml of water and neutralized with 1N aqueous sodium hydroxide solution. The resulting crystals were recovered by filtration and rinsed with a small amount of water. The resulting crystals were suspended in 2 ml of water followed by addition of a stoichiometric amount of 1N-hydrochloric acid and, further, 5 ml of ethanol. The crystals were recovered by filtration and dried under reduced pressure to provide 0.63 g of 6-imidazolyl-7-nitropyrido[2,3-b]pyrazine-2,3-dione hydrochloride.

Physicochemical properties:
NMR (DMSO-$d_6$; δ from TMS): 7.87 (m, 1H), 8.07 (m, 1H), 8.46 (s, 1H), 9.53 (m, 1H), 12.74 (s, 1H), 13.16 (br, 1H).
MS (FAB): 275 (M+ +1).

m.p.: >300° C. (EtOH-H₂O).

| E.A. (for C₁₀H₆N₆O₄.HCl.0.2H₂O): | | | | |
|---|---|---|---|---|
| | C | H | N | Cl |
| Calcd. (%) | 38.22 | 2.37 | 26.74 | 11.28 |
| Found (%) | 38.33 | 2.34 | 26.63 | 11.40 |

EXAMPLE 3

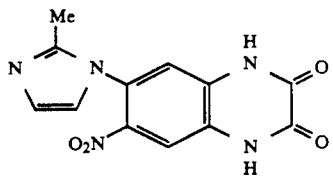

In DMF, 1 g of 6-fluoro-7-nitroquinoxaline-2,3-(1H,4H)-dione and 1.8 g of 2-methylimidazole were stirred with heating at 130° C. for 8 hours. The reaction mixture was then concentrated and diluted with water, whereupon crystals separated out. The crystals were recrystallized from DMF-water to provide 540 mg of 6-(2-methylimidazolyl)-7-nitroquinoxaline-2,3-(1H,4H)-dione.
Physicochemical properties:
NMR (DMSO-$d_6$; δ from TMS): 2.09 (s, 3H), 6.93 (1H), 7.12 (s, 1H), 7.19 (1H), 7.95 (s, 1H), 12.42 (2H).
MS (FAB): 288 (M⁺+1).
m.p.: >300° C. (DMF-H₂O).

| E.A. (for C₁₂H₉N₅O₄.H₂O): | | | |
|---|---|---|---|
| | C | H | N |
| Calcd. (%) | 47.22 | 3.63 | 22.94 |
| Found (%) | 46.64 | 3.57 | 22.59 |

EXAMPLE 4

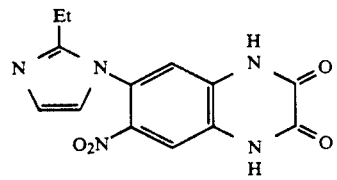

The same procedure as in Example 3 was repeated except 2-ethylimidazole was used in lieu of 2-methylimidazole. As a result, 450 mg of 6-(2-ethylimidazolyl)-7-nitroquinoxaline-2,3-(1H,4H)-dione was obtained.
Physicochemical properties:
NMR (DMSO-$d_6$; δ from TMS): 1.10 (t, 3H), 2.38 (dd, 2H), 6.92 (d, 1H), 7.09 (s, 1H), 7.15 (d, 1H), 7.92 (s, 1H).
MS (FAB): 302 (M⁺+1). m.p.: 249°–250° C. (DMF-H₂O). E.A. (for C₁₃H₁₁N₅O₄.H₂O):

| E.A. (for C₁₃H₁₁N₅O₄.H₂O): | | | |
|---|---|---|---|
| | C | H | N |
| Calcd. (%) | 48.91 | 4.10 | 21.94 |
| Found (%) | 48.61 | 4.00 | 21.75 |

EXAMPLE 5

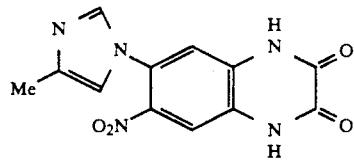

or

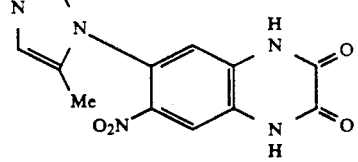

The same procedure as in Example 3 was repeated except 4-methylimidazole was used in lieu of 2-methylimidazole. As a result, 6-(4-methyl-1-imidazolyl)-7-nitroquinoxaline-2,3-(1H,4H)-dione or 6-(5-methyl-1-imidazolyl)-7-nitroquinoxaline-2,3-(1H,4H)-dione was obtained as a single substance with respect to the nuclear magnetic resonance (NMR) spectrum.
Physicochemical properties:
NMR (DMSO-$d_6$; δ from TMS): 2.16 (s, 3H), 7.04 (t, 1H), 7.08 (s, 1H), 7.72 (d, 1H), 7.85 (s, 1H), 12.39 (2H).
MS (FAB): 288 (M⁺+1)
m.p.: >300° C. (DMF-H₂O)

| E.A. (for C₁₂H₉N₅O₄): | | | |
|---|---|---|---|
| | C | H | N |
| Calcd. (%) | 50.18 | 3.16 | 24.38 |
| Found (%) | 49.55 | 3.30 | 23.87 |

EXAMPLE 6

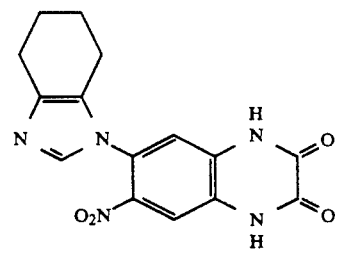

The same procedure as in Example 3 was repeated except 4,5,6,7-tetrahydrobenzimidazole was used in lieu of 2-methylimidazole. As a result, 450 mg of 6-nitro-7-(4,5,6,7-tetrahydro-1-benzimidazolyl)quinoxaline-2,3-(1H,4H)-dione was obtained.
Physicochemical properties:
NMR (DMSO-$d_6$; δ from TMS): 1.70 (4H), 2.18 (2H), 2.50 (2H), 12.35 (2H).
MS (FAB): 328 (M⁺+1).
m.p.: >300° C.;

| E.A. (for $C_{15}H_{13}N_5O_4 \cdot 1.5H_2O$): | | | |
|---|---|---|---|
| | C | H | N |
| Calcd. (%) | 50.85 | 4.55 | 19.77 |
| Found (%) | 50.58 | 4.54 | 19.57 |

EXAMPLE 7

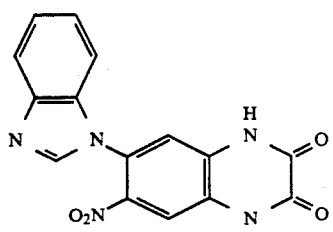

A dry DMSO solution containing 1.2 g of 6-fluoro-7-nitroquinoxaline-2,3-(1H,4H)-dione, 740 mg of potassium hydroxide powder and 1.3 g of benzimidazole was stirred with heating at 130° C. for 5.5 hours. The reaction mixture was then poured in ice-water, followed by addition of hydrochloric acid, and the mixture was filtered at pH about 9 to separate insolubles. The filtrate was then adjusted to pH about 7 with hydrochloric acid, whereupon crystals separated out again. These crystals were collected by filtration to provide 210 mg of 6-(benzimidazol-1-yl)-7-nitroquinoxaline-2,3-(1H,4H)-dione.

Physicochemical properties:
NMR (DMSO-$d_6$; δ from TMS): 7.12–7.39 (4H), 7.73–7.84 (1H), 8.05 (s, 1H), 8.45 (s, 1H), 12.37 (2H).
MS (FAB): 324 (M+ +1).
m.p.: >300° C. (KOHaq-HClaq).

| E.A. (for $C_{15}H_9N_5O_4 \cdot H_2O$): | | | |
|---|---|---|---|
| | C | H | N |
| Calcd. (%) | 52.79 | 3.25 | 20.52 |
| Found (%) | 52.20 | 3.37 | 20.12 |

EXAMPLE 8

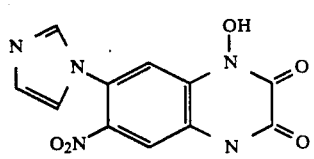

In 5 ml of DMF were dissolved 0.5 g of 7-fluoro-1-hydroxy-6-nitroquinoxaline-2,3-(1H,4H)-dione and 0.7 g of imidazole, and the mixture was stirred with heating at 120° C. for 1.5 hours. After cooling to room temperature, the reaction mixture was diluted with water and adjusted to pH 6 with 1N-hydrochloric acid. The resulting crystals were recovered by filtration, rinsed with water and washed with ethanol to provide 0.33 g of solid matter. This solid was recrystallized from DMF and the resulting crystals were washed with ethanol to provide 0.12 g (20%) of 1-hydroxy-7-imidazolyl-6-nitroquinoxaline-2,3-(1H,4H)-dione.

Physicochemical properties:
NMR (DMSO-$d_6$; δ from TMS): 3.5 (1H), 7.10 (s, 1H), 7.42 (s, 1H), 7.45 (s, 1H), 7.91 (s, 1H), 7.97 (s, 1H), 12.5 (1H).
MS (FAB): 290 (M+ +1).
m.p.: 235° C. (dec.) (DMF).

| E.A (for $C_{11}H_7N_5O_5 \cdot 0.5DMF \cdot 0.5H_2O$): | | | |
|---|---|---|---|
| | C | H | N |
| Calcd. | 44.85 | 3.46 | 23.01 |
| Found (%) | 45.05 | 3.51 | 22.99 |

EXAMPLE 9

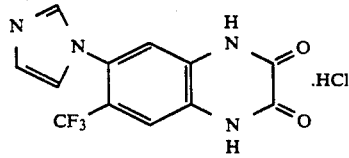

To a solution of 0.50 g of 4-(1-imidazolyl)-2-nitro-5-trifluoromethylaniline in 10 ml of ethanol was added 0.05 g of 10% palladium-on-carbon and hydrogenation was carried out at ordinary temperature and pressure for 30 minutes. The reaction mixture was then filtered and the filtrate was concentrated. To the residue were added 0.17 g of oxalic acid and 15 ml of 4N-hydrochloric acid and the mixture was refluxed for 5 hours. After spontaneous cooling, the resulting crystals were recovered by filtration and rinsed with a small amount of water. The crystals were then dried under reduced pressure to provide 0.14 g of 6-(1-imidazolyl)-7-trifluoromethylquinoxaline-2,3-(1H,4H)-dione hydrochloride hydrate.

Physicochemical properties:
NMR (DMSO-$d_6$; δ from TMS): 7.49 (s, 1H), 7.69 (s, 1H), 7.86 (s, 1H), 8.00 (s, 1H), 9.43 (s, 1H), 12.41 (s, 1H), 12.60 (s, 1H).
MS (FAB): 297(M+ +1).
m.p.: >300° C.

| E.A. (for $C_{12}H_7N_4O_3F_3 \cdot HCl \cdot H_2O$): | | | | |
|---|---|---|---|---|
| | C | H | N | F | Cl |
| Calcd. (%) | 41.10 | 2.87 | 15.98 | 16.25 | 10.11 |
| Found (%) | 41.14 | 2.95 | 15.96 | 16.22 | 10.28 |

EXAMPLE 10

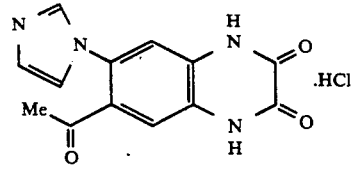

In 30 ml of ethanol was dissolved 0.27 g of 4-amino-2-(1-imidazolyl)-5-nitroacetophenone followed by addition of 0.27 g of Raney nickel, and hydrogenation was carried out at ordinary temperature and pressure for 30 minutes. The reaction mixture was then filtered and the filtrate was concentrated under reduced pressure. To the residue were added 0.10 g of oxalic acid and 12 ml of 4N-hydrochloric acid, and the mixture was refluxed for 5 hours. The reaction mixture was allowed to cool and the resulting crystals were recovered by filtration. The crystals were washed with a small amount of hydrochloric acid and dried under reduced pressure to provide 0.08 g (23%) of 6-acetyl-7-(1-imidazolyl)-quinoxaline-2,3-(1H,4H)-dione hydrochloride 1.5 hydrate.

Physicochemical properties:
NMR (DMSO-d6; δ from TMS): 2.45 (s, 3H), 7.34 (s, 1H), 7.84–7.92 (m, 3H), 9.39 (t, 1H), 12.34 (s, 1H), 12.56 (s, 1H).
MS (FAB): 271 (M+ +1).
m.p.: 285° C. (dec.).

| E.A. (for C13H10N4O3.HCl.1.70 H2O): | | | | |
|---|---|---|---|---|
| | C | H | N | Cl |
| Calcd. (%) | 46.29 | 4.30 | 16.61 | 10.51 |
| Found (%) | 46.22 | 4.20 | 16.52 | 10.69 |

EXAMPLE 11

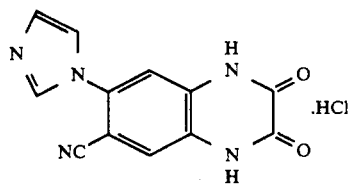

To 20 ml of 1N-hydrochloric acid was mixed 1.6 g of 4-amino-2-(1-imidazolyl)-5-nitrobenzonitrile followed by addition of 0.2 g of 10% palladium-on-carbon, and hydrogenation was carried out. The reaction mixture was filtered and concentrated under reduced pressure. To the residue were added 20 ml of 4N-hydrochloric acid and 0.9 g of oxalic acid, and the mixture was refluxed for 4 hours. The reaction mixture was then allowed to cool to room temperature and the resulting crystals were recovered by filtration and recrystallized from 4N-hydrochloric acid to provide 760 mg of 6-(1-imidazolyl)-7-cyanoquinoxaline-2,3-dione hydrochloride.

Physicochemical properties:
NMR (DMSO-d6; δ from TMS): 7.52 (s, 1H), 7.73 (s, 1H), 7.90 (s, 1H), 8.14 (s, 1H), 9.54 (s, 1H), 12.48 (s, 1H), 12.69 (s, 1H).
MS (FAB): 254 (M+ +1).
m.p.: 300° C. (4N-HCl).

| E.A. (for C12H7N5O2.1HCl): | | | | |
|---|---|---|---|---|
| | C | H | N | Cl |
| Calcd. (%) | 49.76 | 2.78 | 24.18 | 12.24 |
| Found (%) | 49.40 | 2.85 | 23.95 | 12.32 |

EXAMPLE 12

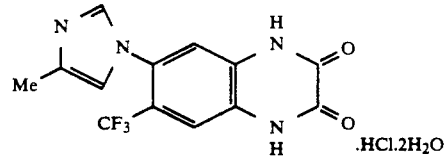

In a mixture of 10 ml of ethanol and 1 ml of concentrated hydrochloric acid was dissolved 0.60 g of 4-[1-(4-methylimidazolyl)]-2-nitro-5-trifluoromethylaniline as synthesized from 4-fluoro-2-nitro-5-trifluoromethylacetanilide and 4-methylimidazole by the procedure described in Reference Example 4. To this solution was added 0.06 g of 10% palladium-on-carbon, and hydrogenation was carried out at ordinary temperature and pressure for 3 hours. The reaction mixture was then filtered and the filtrate was concentrated under reduced pressure. To the residue were added 0.20 g of oxalic acid and 12 ml of 4N-hydrochloric acid, and the mixture was refluxed for 6 hours. After spontaneous cooling, the resulting crystals were recovered by filtration, washed with a small amount of hydrochloric acid and dried under reduced pressure to provide 0.28 g (37%) of 6-[1-(4-methylimidazolyl)]-7-trifluoromethylquinoxaline-2,3-(1H,4H)-dione hydrochloride dihydrate.

Physicochemical properties:
NMR (DMSO-d6; δ from TMS):
2.37 (s, 3H), 7.51 (s, 1H), 7.74 (s, 2H),
9.42 (s, 1H), 12.49 (s, 1H), 12.69 (s, 1H).
MS (FAB): 311 (M+ +1).
m.p.: >300° C.

| E.A. (for C13H9N4O2F3.HCl.2.1 H2O): | | | | | |
|---|---|---|---|---|---|
| | C | H | N | F | Cl |
| Calcd. (%) | 40.61 | 3.72 | 14.57 | 14.82 | 9.22 |
| Found (%) | 40.60 | 3.42 | 14.51 | 14.45 | 9.60 |

EXAMPLE 13

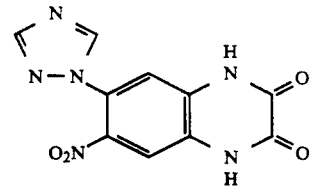

In 5 ml of sulfolane were dissolved 0.5 g of 6-fluoro-7-nitroquinoxaline-2,3-(1H,4H)-dione and 0.65 g of sodium triazole, and the mixture was stirred at 180° C. for 2 hours. The reaction mixture was then diluted with ice-water and neutralized with hydrochloric acid. The resulting crystals were recovered by filtration, washed with water and then with alcohol to provide 470 mg of 6-nitro-7-(1,2,4-triazol-1-yl)quinoxaline-2,3-(1H,4H)-dione.

Physicochemical properties:
NMR (DMSO-d6; δ from TMS): 7.30 (s, 1H), 7.88 (s, 1H), 8.24 (s, 1H), 9.02 (s, 1H), 12.40 (2H).
MS (FAB): 275 (M+ +1).
m.p.: >300° C.

| E.A. (for C₁₀H₆N₆O₄·0.5 H₂O): | | | |
|---|---|---|---|
| | C | H | N |
| Calcd. (%) | 42.41 | 2.49 | 29.68 |
| Found (%) | 42.85 | 2.50 | 29.74 |

EXAMPLE 14

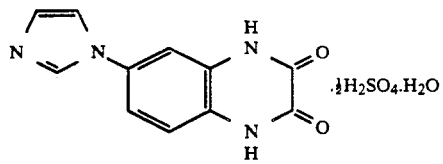

In 4N-hydrochloric acid were dissolved 1.4 g of 4-imidazolyl-1,2-diaminobenzene and 0.9 g of oxalic acid, and the solution was refluxed overnight. After cooling to room temperature, the resulting crystals were recovered by filtration and dissolved in sulfuric acid. The solution was poured in ice-water, whereupon crystals formed again. These crystals were recovered by filtration and dried to provide 0.65 g of 6-imidazolylquinoxaline-2,3-(1H,4H)-dione hemisulfate monohydrate.

Physicochemical properties:
NMR (DMSO-$d_6$; δ from TMS): 7.22–7.36 (2H), 7.42 (d, 1H), 7.52 (s, 1H), 7.90 (s, 1H), 8.90 (s, 1H).
MS (EI): 228 (M+).
m.p.: >300° C. ($H_2SO_4$-$H_2O$).

| E.A. (for C₁₁H₆N₄O₂·½ H₂SO.H₂O): | | | | |
|---|---|---|---|---|
| | C | H | N | S |
| Calcd. (%) | 44.75 | 3.76 | 18.98 | 5.43 |
| Found (%) | 44.85 | 3.77 | 19.07 | 5.38 |

EXAMPLE 15

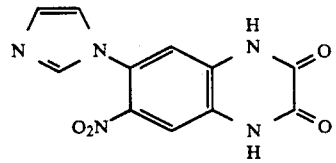

In 5 ml of sulfuric acid was dissolved 0.5 g of 6-imidazolylquinoxaline-2,3-(1H,4H)-dione hydrochloride followed by addition of 0.21 g of potassium nitrate, and the resulting mixture was heated at 70° C. for 5 minutes. After spontaneous cooling to room temperature, the reaction mixture was poured in ice-water and adjusted to pH 4–5 with aqueous sodium hydroxide solution, whereupon crystals separated out. These crystals were recovered by filtration and recrystallized from DMF-water to provide 0.27 g of 6-imidazolyl-7-nitroquinoxaline-2,3-(1H,4H)-dione.

Physicochemical properties:
NMR (DMSO-$d_6$; δ from TMS): 7.28 (s, 1H), 7.50 (s, 1H), 7.82 (s, 1H), 8.02 (s, 1H), 8.68 (s, 1H).
MS (EI): 272 (M++1).
m.p.: >300° C. (DMF-$H_2O$).

| E.A. (for C₁₁H₇N₅O₄): | | | |
|---|---|---|---|
| | C | H | N |
| Calcd. (%) | 48.36 | 2.58 | 25.63 |
| Found (%) | 48.36 | 2.68 | 25.66 |

EXAMPLE 16-1

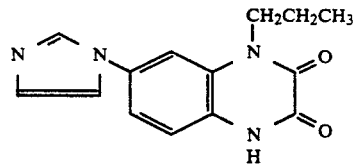

A mixture of 4.2 g of 4-(1-imidazolyl)-2-n-propylaminonitrobenzene, 0.8 g of 10% palladium-on-carbon and 60 ml of 1N-hydrochloric acid was subjected to hydrogenation reaction. The reaction mixture was filtered and the filtrate was concentrated under reduced pressure. To the residue were added 20 ml of 4N-hydrochloric acid and 3 g of oxalic acid, and the mixture was refluxed for 5 hours. After spontaneous cooling to room temperature, the resulting crystals were recovered by filtration and recrystallized from 4N-hydrochloric acid to provide 3 g of 7-(1-imidazolyl)-1-n-propylquinoxaline-2,3-(1H,4H)-dione hydrochloride.

The following compounds were synthesized in the same manner (Examples 16-2 through 16-12).

16-2: 1-Hydroxyethyl-7-(1-imidazolyl)quinoxaline-2,3-(1H,4H)-dione hydrochloride hydrate 16-3: 7-(1-Imidazolyl)-1-(N-morpholino)ethylquinoxaline-2,3-(1H,4H)-dione dihydrochloride 2.5 hydrate 16-4: 7-(1-imidazolyl)-1-(2-tetrahydrofuranyl)methylquinoxaline-2,3-(1H,4H)-dione hydrochloride hydrate 16-5: 1-Decyl-7-(1-imidazolyl)quinoxaline-2,3-(1H,4H)-dione hydrochloride 1.5 hydrate 16-6: 1-(Dimethylamino)ethyl-7-(1-imidazolyl)-quinoxaline-2,3-(1H,4H)-dione dihydrochloride 1.5 hydrate 16-7: 1-(2-Aminocyclohexyl)-7-(1-imidazolyl)quinoxaline-2,3-(1H,4H)-dione dihydrochloride dihydrate 16-8: 7-(1-Imidazolyl)-1-(2,2,6,6-tetramethylpiperidin-4-yl)quinoxaline-2,3-(1H,4H)-dione dihydrochloride trihydrate 16-9: 7-(1-Imidazolyl)-1-methylquinoxaline-2,3-(1H,4H)-dione hydrochloride 16-10: 7-(1-Imidazolyl)-1-cyclohexylquinoxaline-2,3-(1H,4H)-dione hydrochloride hydrate 16-11: 7-(1-Imidazolyl)-1-cyclohexylmethylquinoxaline-2,3-(1H,4H)-dione hydrochloride 1.5 hydrate 16-12: 7-(1-Imidazolyl)-1-isopentylquinoxaline-2,3-(1H,4H)-dione hydrochloride 1.5 hydrate

EXAMPLE 17

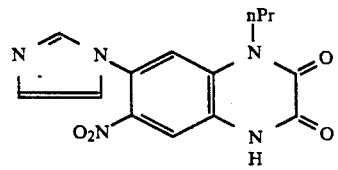

To a solution of 1 g of 7-(1-imidazolyl)-1-n-propyl-quinoxaline-2,3-(1H,4H)-dione hydrochloride in 8 ml of sulfuric acid was added 0.4 g of potassium nitrate, and the mixture was stirred overnight. The reaction mixture was poured in ice-water and adjusted to pH 7. The resulting crystals were recrystallized from 1N-hydrochloric acid to provide 0.9 g of 7-(1-imidazolyl)-6-nitro-1-n-propylquinoxaline-2,3-(1H,4H)-dione hydrochloride.

The following compounds were obtained in the same manner (Examples 17-2 through 17-13).

17-2: 1-Hydroxyethyl-7-(1-imidazolyl)-5-nitroquinoxaline-2,3-(1H,4H)-dione hydrate 17-3: 7-(1-Imidazolyl)-1-(N-morpholino)ethyl-6-nitroquinoxaline-2,3-(1H,4H)-dione hydrate 17-4: 7-(1-Imidazolyl)-1-(N-morpholino)ethyl-5nitroquinoxaline-2,3-(1H,4H)-dione dihydrate 17-5: 7-(1-Imidazolyl)-6-nitro-1-(3-quinuclidinyl)-quinoxaline-2,3-(1H,4H)-dione dihydrate 17-6: 1-Decyl-7-(1-imidazolyl)-6-nitroquinoxaline-2,3-(1H,4H)-dione hydrochloride 17-7: 1-(2-Dimethylamino)ethyl-7-(1-imidazolyl)-6-nitroquinoxaline-2,3-(1H,4H)-dione dihydrochloride 17-8: 1-(2-Aminocyclohexyl)-7-(1-imidazolyl)-6-nitroquinoxaline-2,3-(1H,4H)-dione dihydrochloride 1 isopropyl alcohol 17-9: 7-(1-Imidazolyl)-6-nitro-1-(2,2,6,6-tetramethyl-piperidin-4-yl)quinoxaline-2,3-(1H,4H)-dione 17-10: 7-(1-Imidazolyl)-6-nitro-1-cyclohexylquinoxaline-2,3-(1H,4H)-dione sulfate hydrate 17-11: 7-(1-Imidazolyl)-6-nitro-1-methylquinoxaline-2,3(1H,4H)-dione sodium dihydrate 17-12: 7-(1-Imidazolyl)-6-nitro-1-cyclohexylmethyl-quinoxaline-2,3-(1H,4H)-dione 0.5 hydrate 17-13: 7-(1-Imidazolyl)-6-nitro-1-isopentylquinoxaline-2,3-(1H,4H)-dione sodium salt

EXAMPLE 18

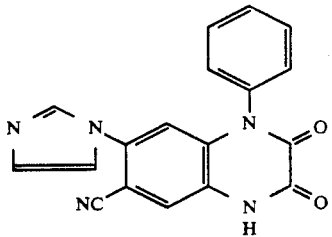

A mixture of 680 mg of 2-(1-imidazolyl)-5-nitro-4-phenylaminobenzonitrile, 200 mg of 10% palladium-on-carbon and 10 ml of 1N-hydrochloric acid was subjected to hydrogenation reaction. The reaction mixture was filtered and the filtrate was concentrated under reduced pressure. To the residue were added 8 ml of 4N-hydrochloric acid and 420 mg of oxalic acid and the mixture was refluxed for 2 hours. After spontaneous cooling to room temperature, the resulting crystals were recovered by filtration and recrystallized from 4N-hydrochloric acid. The crystals were neutralized with sodium hydroxide and rinsed with water to provide 186 mg of 6-cyano-7-(1-imidazolyl)-1-phenyl-quinoxaline-2,3-(1H,4H)-dione hydrate.

The following compounds were synthesized in the same manner. 6-Cyano-7-(1-imidazolyl)-1-(2-carboxyethyl)-quinoxaline-2,3-(1H,4H)-dione hydrate 6-Cyano-7-(1-imidazolyl)-1-(2,2,2-trifluoroethyl)-quinoxaline-2,3-(1H,4H)-dione hydrochloride dihydrate

EXAMPLE 19

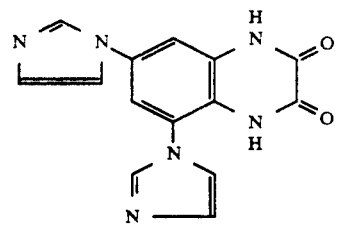

A mixture of 2.5 g of 3,5-di-(1-imidazolyl)-2-nitroaniline dihydrochloride, 300 mg of 10% palladium-on-carbon and 25 ml of 1N-hydrochloric acid was subjected to hydrogenation reaction. The reaction mixture was then filtered and the filtrate was concentrated under reduced pressure. To the residue were added 15 ml of 4N-hydrochloric acid and 900 mg of oxalic acid, and the mixture was refluxed with stirring for 10 hours. The reaction mixture was then concentrated under reduced pressure, dissolved in water and neutralized with sodium hydroxide. The resulting crystals were washed with ethanol-water to provide 870 mg of 5,7-di(1-imidazolyl)quinoxaline-2,3-(1H,4H)-dione.

EXAMPLE 20

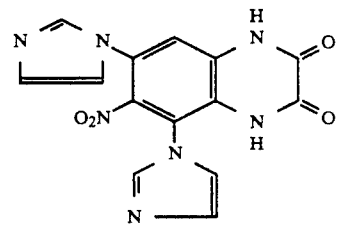

In 3 ml of concentrated sulfuric acid was dissolved 290 mg of 5,7-di-(1-imidazolyl)quinoxaline-2,3-(1H,4H)-dione hydrate followed by addition of 220 mg of potassium nitrate with ice-cooling. After cooling to room temperature, the reaction mixture was further stirred at 80° C. for 30 minutes. After cooling to room temperature, the reaction mixture was poured in ice-water and adjusted to pH 7 with sodium hydroxide. The resulting crystals were recovered by filtration and washed with water to provide 124 mg of 5,7-di(1-imidazolyl)-6-nitroquinoxaline-2,3-(1H,4H)-dione.

EXAMPLE 21

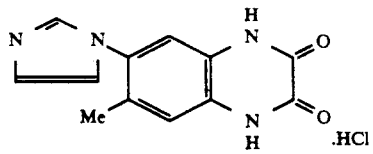

In a mixture of 2 ml of methanol and 1 ml of 1N-hydrochloric acid was dissolved 0.16 g of 4-(1-imidazolyl)-3-methyl-6-nitroaniline, and the solution was subjected to hydrogenation in the presence of 16 mg of 10% Pd-C at ordinary temperature and pressure for 3 hours. The reaction mixture was filtered and the filtrate was concentrated. To the residue were added 46 mg of oxalic acid and 9 ml of 4N-hydrochloric acid, and the mixture was refluxed overnight. After spontaneous cooling of the reaction mixture to room temperature, the resulting crystals were recovered by filtration and recrystallized from water-DMF to provide 25 mg of 6-(1-imidazolyl)-7-methylquinoxaline-2,3-(1H,4H)-dione hydrochloride.

EXAMPLE 22-1

In 40 ml of 4N-hydrochloric acid, 2 g of 5-(1-imidazolyl)-3-(N-morpholino)-2-nitrobenzacetamide was heated for 1 hour, and the reaction mixture was concentrated under reduced pressure. The concentrate was dissolved in 20 ml of 1N-hydrochloric acid followed by addition of 1 g of 10% palladium-on-carbon, and hydrogenation was carried out. The reaction mixture was filtered and the filtrate was concentrated under reduced pressure. To the residue was added 1 g of oxalic acid and the mixture was dissolved in 12 ml of 4N-hydrochloric acid. The reaction mixture was refluxed for 5 hours, after which it was allowed to cool to room temperature and the resulting crystals were recovered by filtration to provide 1.7 g of 7-(1-imidazolyl)-5-(N-morpholino)quinoxaline-2,3-(1H,4H)-dione dihydrochloride 1.5 hydrate.

EXAMPLE 22-2

In a mixture of 15 ml of acetic anhydride, 3 ml of acetic acid and 2 ml of sulfuric acid was dissolved 1.5 g of 7-(1-imidazolyl)-5-(N-morpholino)quinoxaline-2,3-(1H,4H)-dione followed by addition of 0.33 ml of fuming nitric acid at a temperature not exceeding 10° C. The mixture was allowed to stand at room temperature for 1 hour, after which it was concentrated. The concentrate was diluted with ice-water and adjusted to pH 7 with alkaline solution. The mixture was then purified with HP-20 resin to provide 600 mg of 6-(1-imidazolyl)-8-(N-morpholino)-5-nitroquinoxaline-2,3-(1H,4H)-dione hydrate.

REFERENCE EXAMPLE 7

To a mixture of 6.2 g of 2-ethoxalylamino-4-fluoronitrobenzene and 124 ml of DMF was added a solution of 5.64 g of ammonium chloride in 40 ml of water. Then, 5.7 g of zinc dust was added in small portions to the above mixture. The reaction mixture was stirred under TLC (5% methanol-chloroform) monitoring and, when the starting material had disappeared, the mixture was filtered using Celite and washed with hot DMF. The mixture was heated at 100° C. for 3 hours, after which it was ice-cooled and the resulting inorganic salt crystals were filtered off. To the organic layer was added methanol and the resulting crystals were recovered by filtration to provide 2.73 g of 6-fluoro-1-hydroxyquinoxaline-2,3-(1H,4H)-dione.

REFERENCE EXAMPLE 8

In 22 ml of sulfuric acid was dissolved 1.6 g of 6-fluoro-1-hydroxyquinoxaline-2,3-(1H,4H)-dione followed by addition of 0.9 g of $KNO_3$. The mixture was reacted at room temperature for 3 hours, after which it was poured in ice-water. The resulting crystals were recovered by filtration to provide 310 mg of 6-fluoro-1-hydroxy-7-nitroquinoxaline-2,3-(1H,4H)-dione.

EXAMPLE 23

A mixture of 1 g of 4,5-di-(1-imidazolyl)-2-nitroaniline dihydrochloride, 5 ml of acetic acid, 5 ml of methanol and 0.1 g of 10% palladium-on-carbon was subjected to hydrogenation reaction. The reaction mixture was filtered and the filtrate was washed with hydrochloric acid and concentrated under reduced pressure. The concentrate was dissolved in 350 mg oxalic acid-6 ml of 4N-hydrochloric acid and the solution was subjected to dry distillation overnight. The resulting crystals were recovered by filtration and recrystallized from 4N-hydrochloric acid to provide 170 mg of 6,7-di-(1-imidazolyl)quinoxaline-2,3-(1H,4H)-dione dihydrochloride dihydrate.

EXAMPLE 24

A mixture of 1.3 g of 4-fluoro-5-(1-imidazolyl)-2-nitroaniline hydrochloride, 20 ml of ethanol, 75 mg of platinum oxide and 0.5 ml of concentrated hydrochloric acid was subjected to hydrogenation reaction. The reaction mixture was filtered and washed with hydrochloric acid-ethanol. The filtrate was concentrated under reduced pressure, the concentrate was dissolved in 1 g oxalic acid-20 ml 4N-hydrochloric acid, and the mixture was refluxed for 3 hours. The resulting crystals were recovered by filtration and recrystallized from 1N-hydrochloric acid to provide 900 mg of 6-fluoro-7-(1-imidazolyl)quinoxaline-2,3-(1H,4H)-dione hydrochloride hydrate.

EXAMPLE 25

A mixture of 370 mg of 6-fluoro-1-hydroxy-7-nitroquinoxaline-2,3-(1H,4H)-dione, 320 mg of imidazole and 37 ml of DMF was stirred at 100° C. for 4 hours. The reaction mixture was concentrated and, then, diluted with water. The aqueous layer was neutralized with hydrochloric acid and the resulting crystals were recovered by filtration and washed with water to provide 214 mg of 1-hydroxy-6-(1-imidazolyl)-7-nitroquinoxaline-2,3-(1H,4H)-dione ½ hydrate.

EXAMPLE 26

In 10 ml of 1N-hydrochloric acid was dissolved 0.5 g of 4-(1-imidazolyl)-2-nitro-5-trifluoromethyl-N-propylaniline followed by addition of 50 mg of 10% palladium-on-carbon, and hydrogenation reaction was carried out. The reaction mixture was filtered and the filtrate was washed with water and concentrated under reduced pressure. The residue was dissolved in 250 mg oxalic acid-6 ml 4N-hydrochloric acid and the solution was refluxed. The resulting crystals were filtered off and the mother liquor was neutralized with 1N aqueous solution of sodium hydroxide. The resulting crystals were recovered by filtration to provide 110 mg of 6-(1-imidazolyl)-1-propyl-7-trifluoromethylquinoxaline-2,3-(1H,4H)-dione hydrate.

EXAMPLE 27

The same procedure as in Example 3 was repeated except 4-phenylimidazole was used in lieu of 2-methylimidazole. As a result, 270 mg of 6-nitro-7-(4-phenylimidazol-1-yl)quinoxaline-2,3-(1H,4H)-dione hydrate was obtained.

EXAMPLES 17-14

1-(2-Acetoxyethyl)-7-(1-imidazolyl)-6-nitroquinoxaline-2,3-(1H,4H)-dione hydrate

EXAMPLES 17-15

In 5 ml of 4N-hydrochloric acid was dissolved 250 mg of 1-(2-acetoxyethyl)-7-(1-imidazolyl)-6- nitroquinoxaline-2,3-(1H,4H)-dione of Example 17-14 and the solution was stirred at 100° C. for 3 hours. The reaction mixture was concentrated, followed by addition of methanol, whereupon crystals separated out. The crystals were recovered by filtration to provide 200 mg of 1-(2-hydroxyethyl)-7-(1-imidazolyl)-6-nitroquinoxaline-2,3-(1H,4H)-dione hydrochloride.

EXAMPLES 17-16

7-(1-Imidazolyl)-6-nitro-1-(3-pyrrolidinyl)-quinoxaline-2,3-(1H,4H)-dione

EXAMPLE 28

The same procedure as in Example 3 was repeated except 4-nitroimidazole was used in lieu of 2-methylimidazole. As a result, 100 mg of 6-nitro-7-(4-nitroimidazol-1-yl)quinoxaline-2,3-(1H,4H)-dione was obtained.

EXAMPLE 29

| Freeze-dried preparation In each vial: | |
| --- | --- |
| Compound of Example 15 or 9 | 50 mg (0.5%) |
| Citric acid | 210 mg (2.1%) |
| D-Mannitol | 100 mg (1.0%) |
| | 10 ml |

In 800 ml of water are serially dissolved 5 g of the compound of Example 15 or 9, 21 g of citric acid and 10 g of D-mannitol, followed by addition of sufficient water to make the solution 1000 ml. This solution is aseptically filtered and the filtrate is filled, in 10 ml portions, into amber-colored vials and freeze-dried to provide an injectable preparation which is reconstituted for use.

We claim:

1. A pyrazine derivative represented by the general formula:

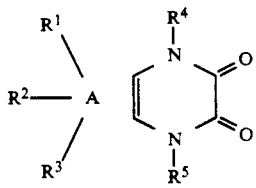

wherein ring A represents a benzene ring of the formula

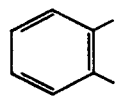

or a pyridine ring of the formula

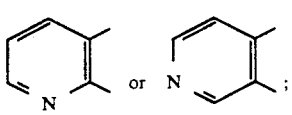

$R^1$ represents

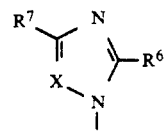

(X represents a nitrogen atom, or a carbon atom substituted by $R^8$, $R^6$ represents a hydrogen atom or a lower alkyl group, $R^7$ and $R^8$ are the same or different and each represents hydrogen, lower alkyl, nitro or phenyl, or $R^7$ and $R^8$ are combined together to represent butadienylene (—CH=CH—CH=CH—) or 1,4-butylene (—CH$_2$—CH$_2$—CH$_2$—CH$_2$—)); $R^2$ and $R^3$ are the same or different and each represents hydrogen, fluoro, cyano, lower acyl, nitro, unsubstituted or fluorine-substituted lower alkyl, morpholino, or one of said species of $R^1$ which may be either the same as or different from $R^1$; $R^4$ and $R^5$ are the same or different and each represents hydrogen, hydroxyl, $C_{1-10}$ straight-chain or branched alkyl, $C_{5-8}$ cycloalkyl which may be substituted by amino, a nitrogen-containing 5- or 6-membered heterocyclic group which may be substituted by lower alkyl and which may be bridged by 1 to 3 methylene group(s), phenyl, or Y-substituted $C_{1-6}$ straight-chain or branched alkyl; Y represents hydroxyl, lower acyloxy, fluorine-substituted methyl, $C_{5-8}$ cycloalkyl, tetrahydrofuryl, carboxyl, lower alkoxycarbonyl, or

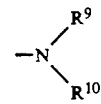

($R^9$ and $R^{10}$ are the same or different and each represents hydrogen or lower alkyl, or alternatively $R^9$ and $R^{10}$ are combined together to represent a 5- or 6-membered cyclic group which may contain oxygen), or a pharmaceutically acceptable salt thereof.

2. The pyrazine derivative as claimed in claim 1 wherein one of $R^2$ and $R^3$ is hydrogen and the other group is hydrogen, trifluoromethyl, cyano, lower alkyl or nitro; $R^4$ and $R^5$ are the same or different and each is hydrogen or hydroxyl; and $R^7$ and $R^8$ are the same or different and each is hydrogen or lower alkyl, or $R^7$ and $R^8$ are combined together to represent butadienylene (—CH=CH—CH=CH—) or 1,4-butylene (—CH$_2$—CH$_2$—CH$_2$—CH$_2$—)).

3. The pyrazine derivative as claimed in claim 2, wherein X is a carbon atom substituted by $R^8$.

4. The pyrazine derivative as claimed in claim 3, wherein one of $R^2$ and $R^3$ is hydrogen and the other group is hydrogen or nitro; and each of $R^4$ and $R^5$ is hydrogen.

5. The pyrazine derivative as claimed in claim 4, wherein A is a benzene group of the formula

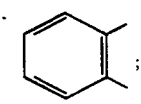

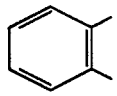

and each of $R^6$, $R^7$, and $R^8$ is hydrogen.

6. The pyrazine derivative as claimed in claim 3, which is 1-hydroxy-7-imidazolyl-6-nitroquinoxaline-2,3-(1H,4H)-dione.

7. The pyrazine derivative as claimed in claim 3, which is 6-(1-imidazolyl)-7-trifluoromethylquinoxaline-2,3-(1H,4H)-dione.

8. The pyrazine derivative as claimed in claim 5, which is 6-imidazolyl-7-nitroquinoxaline-2,3-(1H,4H)-dione.

9. A pharmaceutical composition comprising a therapeutically effective amount of a pyrazine derivative as claimed in claim 1 or a pharmaceutically acceptable salt thereof and a pharmaceutically acceptable carrier.

10. A method for treating a host in need of glutamate receptor antagonizing activity comprising administration to said host a therapeutically effective amount of the pharmaceutical composition of claim 9.

11. The method of claim 10 wherein the pharmaceutical composition is administered in a dosage of from 1 to 1000 mg.

12. The method of claim 10 wherein the pyrazine derivative is 1-hydroxy-7-imidazolyl-6-nitroquinoxaline-2,3-(1H,4H)-dione.

13. The method of claim 10 wherein the pyrazine derivative is 6-(1-imidazolyl)-7-trifluoromethylquinoxaline-2,3-(1H,4H)-dione.

14. The method of claim 10 wherein the pyrazine derivative is 6-imidazolyl-7-nitroquinoxaline-2,3-(1H,4H)-dione.

* * * * *